US008143580B1

(12) United States Patent
Wong

(10) Patent No.: US 8,143,580 B1
(45) Date of Patent: Mar. 27, 2012

(54) CROSSED BIASED FILTERING NDIR GAS SENSING METHODOLOGY

(76) Inventor: Jacob Y Wong, Goleta, CA (US)

( * ) Notice: Subject to any disclaimer, the term of this patent is extended or adjusted under 35 U.S.C. 154(b) by 32 days.

(21) Appl. No.: 12/848,832

(22) Filed: Aug. 2, 2010

Related U.S. Application Data

(63) Continuation-in-part of application No. 12/759,603, filed on Apr. 13, 2010, now Pat. No. 8,003,944.

(60) Provisional application No. 61/273,417, filed on Aug. 3, 2009, provisional application No. 61/212,713, filed on Apr. 14, 2009.

(51) Int. Cl.
*G01J 5/02* (2006.01)
(52) U.S. Cl. .................. 250/339.13; 250/338.5
(58) Field of Classification Search .............. 250/339.13, 250/338.5
See application file for complete search history.

(56) References Cited

U.S. PATENT DOCUMENTS 4,271,124 A * 6/1981 Speeter ...................... 422/82.09
5,886,348 A * 3/1999 Lessure et al. ........... 250/339.13

* cited by examiner

*Primary Examiner* — David Porta
*Assistant Examiner* — Hugh H Maupin
(74) *Attorney, Agent, or Firm* — Wagner, Anderson & Bright, P.C.; Roy L. Anderson

(57) ABSTRACT

An NDIR gas sensor methodology for the design of a dual-gas sensor for the detection of two gases having a mutually interfering infrared absorption band such as that for $CO_2$ and $H_2O$ at around 2.70μ or $N_2O$ and CO at around 4.40μ. The output of this two-channel NDIR gas sensor remains drift-free over time and is also temperature independent because it uses three detection channels sharing the same sample chamber and all have exactly the same narrow band-pass filter. The first detection channel is filled with 100% nitrogen and its output is proportional to the concentration levels for both $CO_2$ and $H_2O$ in the sample chamber. The second detection channel has two cells in series, one filled with a known concentration of $H_2O$ and another one with 100% $CO_2$ gas, and its output is proportional principally only to the presence of $H_2O$ in the sample chamber. The third detection channel is filled with 100% $CO_2$ gas and its output serves as the biased reference for this dual-gas NDIR gas sensor. Outputs from the three detection channels are used to produce a calibration curve for the combined presence of $CO_2$ and $H_2O$ in the sample chamber and also a $CO_2$-independent calibration curve for $H_2O$ for generating a methodology for determining simultaneously the concentration of both $CO_2$ and $H_2O$ in the sample chamber.

17 Claims, 8 Drawing Sheets

CROSSED BIASED FILTERING NDIR GAS SENSING METHODOLOGY

CROSS REFERENCE TO RELATED APPLICATIONS

This application claims the benefit of U.S. Patent Application Ser. 61/273,417, filed Aug. 3, 2009, the disclosure of which is specifically incorporated herein by reference. This application is also a continuation-in-part of U.S. patent application Ser. No. 12/759,603, filed Apr. 13, 2010, now U.S. Pat. No. 8,003,944 which claims the benefit of 61/212,713, filed on Apr. 14, 2009, the disclosures of which are specifically incorporated herein by reference.

FIELD OF THE INVENTION

The present application is in the field of gas analysis, and specifically relates to using a Non-Dispersive Infrared (NDIR) gas analysis technique to determine the concentration of a particular type of gas present in a chamber by sensing the absorption of infrared radiation passing through the gas.

BACKGROUND OF THE INVENTION

Non-Dispersive Infrared (NDIR) gas sensors have been in existence for over six decades—ever since the technology for the fabrication of spectral thin film narrow band pass filters was declassified by the United States government in the late 1940's. Although numerous gas detection methodologies have been developed in parallel over the same time span, the most notable ones include electrochemical fuel cells, Figaro or tin oxide ($SnO_2$) sensors, metal oxide semiconductor (MOS) sensors, catalytic (platinum bead) sensors, photo-ionization detectors (PID), flame-ionization detectors (FID), thermal conductivity sensors etc., all of which are commonly referred to as "interactive" types of gas detectors. As interactive types of gas sensors, almost every such detector without exception suffers from long-term drifts and non-specificity problems.

NDIR gas sensors, on the other hand, have long been considered as one of the best methods for gas measurement since the 1950's. Comparatively speaking, in addition to being highly specific, NDIR gas analyzers are also very sensitive, fast responding, relatively stable over time, rugged, reliable and easy to maintain. A superior gas measurement technique, which only became fully developed within the past two decades, is the tunable diode laser absorption spectroscopy (TDLAS) methodology. This technique uses the output of a laser as a tunable coherent radiation source. TDLAS gas sensors in general possess better gas detection sensitivity, and in some cases, can be more compact and reliable than the corresponding NDIR counterparts. However, due to available laser wavelength restrictions, they have to depend upon the much weaker higher harmonics of the fundamental absorption bands of gases that they detect. Consequently, TDLAS gas sensors routinely require many times the path lengths required for their NDIR counterparts for attaining comparable detection sensitivities and they are, at least at the present time, a lot more expensive because of the limited availability of lasers (particularly of the Quantum Cascade types).

The over six decades of incessant technology development for NDIR gas sensors began with the advent of the "Single Beam Methodology" exemplified by the Beckman LB-1 medical $CO_2$ sensor circa 1951-1955 which suffered from extremely poor output drift problems over temperature and time. The emergence of a variety of "Double Beam Methodology" took place during the period between the early 1960's and the mid-1970's, most notably represented by the development of Hewlett-Packard's Model 47210A Capnometer™ which was also a medical $CO_2$ sensor for monitoring the end-tidal $CO_2$ levels of cardiac and respiratory patients in ICU's (see Jaffe, M B "Infrared measurement of Carbon Dioxide in the Human Breath: "Breathe-Through Devices from Tyndall to the Present Day "*Technology, Computing and Simulation* 2008; 107: 890-904). In the Capnometer, a novel double beam technique known as "Negative Filtering" was advanced in the creation of a two-beam ratio signal processing scheme. This "Double Beam Methodology" was later improved by Burch et al. in U.S. Pat. No. 3,793,525 (1974) and by Blau Jr. in U.S. Pat. No. 3,811,776 (1974) in manners very similar to the "Negative Filtering" concept first introduced in the Hewlett-Packard's Capnometer.

As the fabrication technology for narrow band pass interference filters gradually advanced towards the end of the 1970's, gas cells that were used earlier for implementing NDIR Double Beam methodologies were quickly replaced by these filters. A simpler and less costly Double Beam methodology would involve a beam of infrared energy emanating from an infrared source and passing through a sample chamber containing an unknown amount of the gas whose concentration is to be determined. Before reaching an infrared detector, the beam was passed through two narrow band-pass filters which were mounted on a rotating wheel. One of the two filters would pass only radiation at the characteristic absorption wavelength of the gas to be detected. The other filter was used as a reference filter at a wavelength close to, but not overlapping, that of the first filter. This type of NDIR gas analyzer implementing the Double Beam methodology required generation of some type of synchronizing signal in order to coordinate operation of the signal processing circuit with rotation of the filter wheel.

The period from the early 1980's to the early 1990's witnessed a rapid growth of diverse applications in the use of NDIR gas sensors. Besides the medical and HVACR industries which have been the mainstay for the need of NDIR gas sensors throughout the 1970's, other industries, such as mining, oil and gas production, diverse manufacturing, pharmaceutical etc., where safety and efficiency are invariably of the utmost importance, started to demand more and more NDIR gas sensors. Their demand did not focus just on the general availability in numbers and their detection of diverse gases, but also in the size and ruggedness for these sensors. Throughout the 1970's NDIR gas sensors, especially those that implemented the Double Beam methodology of gas measurement, were bulky, relatively heavy and included moving parts such as mechanical light choppers. Beginning in the mid-1980's, researchers and developers of NDIR gas sensors concentrated on new sensor designs that were compact, lightweight and possessed no mechanical moving parts nor focusing optics. Such designs can be found in U.S. Pat. No. 5,026,992 entitled "Spectral Ratioing Technique for NDIR Gas Analysis Using a Differential Temperature Source" by Wong (Jun. 25, 1991), in U.S. Pat. No. 5,340,986 entitled "Diffusion-Type Gas Sample Chamber" by Wong (Aug. 23, 1994) and in U.S. Pat. No. 5,341,214 entitled "NDIR Gas Analysis Using Spectral Ratioing Technique" by Wong (Sep. 23, 1994).

One of the most noteworthy new designs for NDIR gas sensors was disclosed in U.S. Pat. No. 5,163,332 entitled "Gas Sample Chamber" by Wong (Nov. 17, 1992). A diffusion-type gas sample chamber for use in a gas sensor consists of an elongated hollow tube having an inwardly-facing specularly-reflective surface that permits the tube to function also as a light pipe for transmitting radiation from a source to a detector through the sample gas. A number of filtering apertures in the wall of the otherwise non-porous hollow tube permit the sample gas to enter and exit freely under ambient pressure. This invention for a simplified diffusion-type gas sample chamber provides a novel approach for reducing the complexity of NDIR gas measurement systems by eliminating the need for expensive optics, mechanical choppers and a pump for pulling or pushing the gas into the sample chamber. In addition, the sample chamber of this invention provides a long effective path length which increases the gas detection sensitivity.

From the mid-1990's onwards as the need and use of NDIR gas sensor for detecting all manners of gases in diverse industries continued to grow unabated and the research and development efforts concentrated in new designs that would not only improve their performance characteristics but also reduce the overall sensor cost with the use of multi-channel gas sensors. Many manufacturers took advantage of the so-called waveguide hollow tube sample chamber concept (see U.S. Pat. No. 5,163,332 cited above) and were able to introduce NDIR gas sensors that were significantly lower in unit price. New sensor designs that continued to take advantage of achievements discussed above can be found in U.S. Pat. No. 5,222,389 entitled "Multi-Channel Gas Sample Chamber" by Wong (Jun. 29, 1993) and in U.S. Pat. No. 5,502,308 entitled "Diffusion-Type Gas Sample Chamber" by Wong (Mar. 26, 1996).

In the first of these two disclosed new designs, several detectors equipped with different narrow band-pass interference filters as windows are mounted at the detector end of the so-called waveguide hollow tube sample chamber (see U.S. Pat. No. 5,163,332). By virtue of the fact that the waveguide sample chamber serves as a light pipe to conduct radiation via multiple reflections inside the highly reflective wall, the entire sample chamber is uniformly illuminated with radiation at a slowly decreasing intensity towards the detector end. Thus, at the detector end each of the several mounted detectors essentially receives the same radiation intensity from the common infrared source. Furthermore, each of the common source-detector pair has approximately the same path-length. Thus, if each of the several mounted detectors carries a different narrow band-pass filter that passes radiation which is absorbed by a particular gas present in the gas sample chamber, this new design essentially functions as a compact and low-cost multi-channel NDIR gas sensor.

In the second of the above disclosed new designs, a gas filter cell, inserted to the source/detector end of the waveguide sample chamber (see U.S. Pat. No. 5,341,214), is used to significantly reduce the influence of an interference gas present in the sample chamber. Since the radiation source in this new design is mounted at the same end of the sample chamber as the detector, radiation emitted by the source is reflected from the other end of the sample chamber back to the detector after passing through the gas filter cell twice. The gas filter gas is filled with the interfering gas. In passing twice through the gas filter cell, the radiation generated by the source is greatly attenuated at wavelengths corresponding to the absorption bands of the interfering gas. Since interference occurs only at wavelengths where the absorption bands of the interfering gas overlap the absorption bands of the gas to be detected, the great attenuation of the radiation at such wavelengths by the gas filter cell substantially eliminates the possibility of interference.

New NDIR gas sensor designs continued to be introduced well into the 2,000's aimed at further improving sensor performance and reducing unit production cost for NDIR gas sensors. In U.S. Pat. No. 7,259,374, entitled "Method for Detecting a Gas species Using a Super Tube Waveguide" by Wong (Aug. 21, 2007), the concept of using a hollow tube with an inwardly-facing specularly-reflecting surface as a functionally efficient sample chamber was extended from a one-dimensional straight tube to a multi-bend waveguide collectively greater than 180 degrees in three dimensions. By so doing, the effective sample chamber path length of NDIR gas sensors can be elongated by more than an order of magnitude to 60" or longer. This new design can allow NDIR gas sensors to detect gas concentrations down to 1 ppm or less.

Another noteworthy new design for NDIR gas sensors was recently disclosed in U.S. Pat. No. 7,358,489 entitled "Ultra Low Cost NDIR Gas Sensors" by Wong (Apr. 15, 2008). In this new design, the concentration of a gas species is detected by using a single beam NDIR gas sensor in which an infrared source element is driven at two different temperatures. A feedback loop is designed to sense an operational voltage of the source. A differential gain amplifier is further designed to create a high cycle amplified output and a low cycle amplified output during respectively a high and low cycle pulsing of the source. Meanwhile a controller is used to synchronize the source driver so that a signal processor can determine the gas concentration through the use of the high and low cycle amplified outputs. This new methodology could further afford the use of a non-genuine blackbody source such as an incandescent miniature light bulb in order to minimize the unit production cost for this sensor.

Despite the over six decades of incessant technology development for NDIR gas sensors, there are still two important sensor performance deficiencies that have yet to be overcome. The first one is sensor output stability over time and the second one is sensor output inaccuracies due to other gases present with the gas to be measured because of interferences caused by the overlapping of their absorption bands. One of the most important sensor performance characteristics is indeed the sensor output stability over time without the need for periodic re-calibration. It is because of the fact that without an output stable $CO_2$ controller, for example, the implementation and practice of Demand Controlled Ventilation (DCV) strategy in office and commercial buildings to save energy would be very awkwardly inconvenienced. However, until the middle of the 1990's, no design was yet in sight to remedy this serious deficiency for NDIR gas sensors. It appeared that the only interim solution for solving this problem was through use of sensor output correction software.

Such a sensor was disclosed in U.S. Pat. No. 5,347,474 (1994) entitled "Self-Calibration of an NDIR Gas Sensor" by Wong. This methodology is based upon the concept that some cyclic variables include within each cycle a value that can be extrinsically determined. In such a case, the sensed value may differ from the known value by an amount that is a combination of long-term drift of the sensor and random measuring error. The drift component can however be evaluated and eliminated by devising a specific method as follows. Once each cycle, for a number of cycles, the sensor measures the variable at a time when its value should equal the extrinsically-known value. The differences are plotted versus time, and a best-fitting straight line is determined, which indicates the drift. Throughout the next cycle as the variable is continuously sensed, the drift determined from the best-fitting straight line is continuously applied in small quantities in order to correct the sensed value.

However, this application builds upon U.S. patent application Ser. No. 12/759,603, wherein a new NDIR gas sensing methodology is advanced which renders to first order the output of an NDIR gas sensor designed using this methodology virtually drift-free in time without the need for any sensor output correction software or periodic re-calibration. Thus, it appears that the first and important sensor performance deficiency has now been overcome.

But the second and important sensor performance deficiency, namely cross interferences among gases in a sample when the concentration level of only one of them is of interest to be detected or measured, remains unresolved. Among the most well known examples of such instances are the overlapping of the 2.70μ absorption bands of $CO_2$ and $H_2O$. For this reason, the 4.2μ absorption band of $CO_2$ gas is preferred for the detection of CO2 instead of the 2.70μ absorption band. Since $H_2O$ is always present in the ambience at various unpredictable levels, its interference on $CO_2$ measurement in the ambience would cause unacceptable inaccuracies. Similarly, the 2.70μ absorption band for $H_2O$ cannot be used to detect this gas due to the interference by $CO_2$ and its variable and unpredictable amount normally found in ambient air. This application specifically addresses this performance deficiency and provides a cure for it.

SUMMARY OF THE INVENTION

The present invention is generally directed to an NDIR gas sensor and method of utilizing it in which the NDIR gas sensor has an infrared source compartment containing an infrared source, a sample chamber, a detector compartment having three detection channels, the first detection channel being hermetically sealed with a non-absorbing gas and having a first output modulated by presence of a first gas to be detected and water vapor in the sample chamber, the second detection channel having a chamber hermetically sealed with the first gas and a water cell and having a second output independent of any amount of the first gas in the sample chamber and partially responsive to the amount of the water vapor in the sample chamber, the third detection channel being hermetically sealed with the first gas and having a third output that is independent of the amount of the first gas in the sample chamber, all three of the detection channels having a narrow band pass filter with a central wavelength and a full width half-maximum bandwidth that are identical and the central wavelength falls within an absorption band of the first gas and water vapor, and electronics for processing signals from the three detection channels and for calculating the concentration of the first gas in the gas sample based upon the three outputs and a set of calibration data for the NDIR gas sensor.

In a first, separate group of aspects of the present invention, the set of calibration data is a calibration curve A that plots a ratio of the first output divided by the second output against the first gas concentration alone in the sample chamber, a calibration curve B that plots a ratio of the first output divided by the second output against water vapor concentration alone in the sample chamber, and a calibration curve C that plots a ratio of the third output divided by the second output against water vapor concentration alone in the sample chamber. Calibration curves A and B can be normalized to obtain calibration curves NA and NB, respectively, and when such calibration curves are multiplied together, they form a calibration curve ND.

In a second, separate group of aspects of the present invention, the concentration of the first gas in the gas sample containing water vapor is calculated by obtaining a value "a" for the gas sample as the first output, a value "b" for the gas sample as the second output, a value "c" for the gas sample as the third output, and then normalizing the first output value "a" to obtain a normalized first output value "a'" (value "a" is normalized by dividing value "a" by a value "$a_0$" obtained as the first output when the non-absorbing gas (e.g., nitrogen) alone is present in the sample chamber), dividing the third output value "c" by the second output value "b" to obtain a value "d", using the value "d" and the calibration curve C to obtain a water vapor content "e" in the gas sample, using the water vapor content "e" and the calibration curve NB to obtain a value "f", dividing the value "a'" by the value "f" to obtain a value "g", and using a calibration curve ND and the value "g" to obtain the detected concentration of the first gas in the gas sample.

It is therefore a primary object of the present invention to advance a new design for an NDIR gas sensor and methodology aimed at allowing detection of a gas in a sample when the gas has a strong absorption band overlapping a strong absorption band of water vapor.

This and further objects and advantages will be apparent to those skilled in the art in connection with the drawings and the detailed description of the invention set forth below.

DETAILED DESCRIPTION OF THE INVENTION

Figure 1:
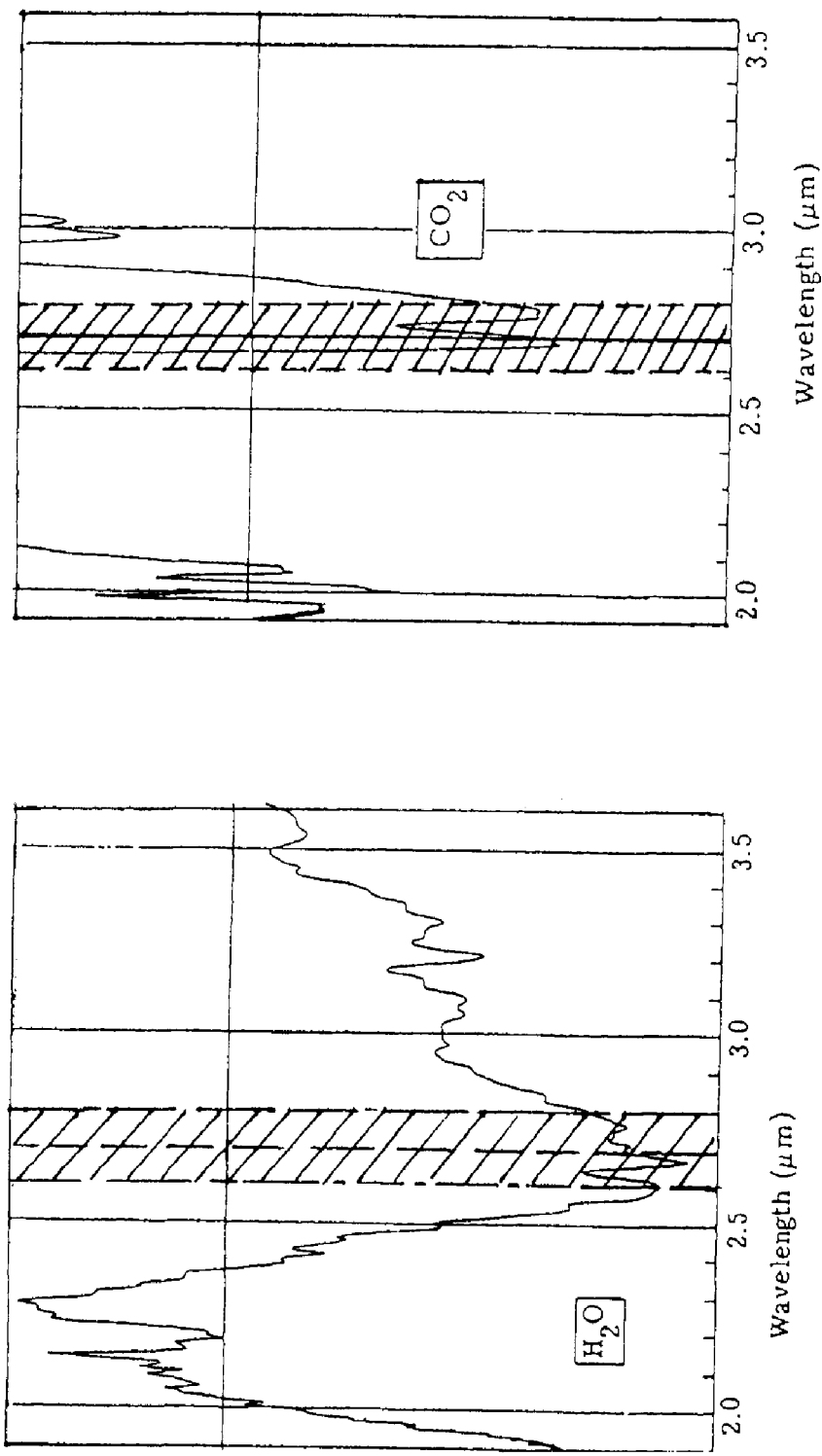
FIG. 1 depicts the infrared absorption bands of CO2 and $H_2O$ around 2.70μ and a narrow band pass spectral filter at 2.70μ used to detect these gases.

The present invention advances NDIR gas sensor methodology by improving an earlier disclosed invention disclosed in U.S. Ser. No. 12/759,603, whereby such a methodology could be applied to the use of a single narrow spectral pass band within which two gases have overlapping strong absorptions. This novel methodology negates the normal interference effects encountered in such a situation and makes possible the simultaneous detection of both of these gases using just a single narrow spectral pass band.

Examples of two gases having strong overlapping absorption bands are $CO_2$ and $H_2O$ at ~2.70μ and also $N_2O$ and CO at ~4.40μ. The present invention advances an NDIR gas sensor methodology for the design of a dual-channel sensor for the detection of two gases having strong but mutually interfering infrared absorption bands such as the examples cited above. Without the present novel methodology, interferences encountered by both gases arising from their spectrally overlapping absorption bands for their detection utilizing conventional NDIR technique would render such a gas sensor design impossible.

The presently invented Crossed Biased Filtering (CBF) NDIR gas sensor methodology utilizes three detection channels all carrying exactly the same narrow band pass spectral filter having the same central wavelength (CWL) at $\lambda_c$ and a full width half-maximum (FWHM) pass bandwidth $B\lambda_C$. An example of this methodology when applied to the detection of both CO2 and $H_2O$ gases uses a $\lambda_c$ and $B\lambda_c$ equal to 2.70µ and 0.20µ, respectively. Another example of this methodology when applied to the detection of both $N_2O$ and CO gases uses a $\lambda_c$ and $B\lambda_c$ equal to 4.40µ and 0.20µ, respectively. The methodology is exactly the same for both examples except for the fact that the formation of the so-called "crossed reference detection channel" or the second detection channel is unique for $H_2O$ gas as compared to other gases such as $N_2$, $N_2O$, CO or $CO_2$ because a 100% concentration of such gases can be readily obtained whereas a 100% concentration cannot be readily obtained for $H_2O$ gas.

The first detection channel, in an especially preferred embodiment hereinafter described, comprises a thermopile detector packaged in a regular TO-18 can hermetically filled with 100% nitrogen. The common narrow band pass spectral filter forms a hermetic window for the regular TO-18 detector package. The output of this first detection channel is modulated by the presence of both $CO_2$ and $H_2O$ gas in the sample chamber.

The second detection channel or the so-called "crossed reference detection channel" comprises a thermopile detector packaged in the same custom-designed "tall" TO-18 can hermetically filled with 100% $CO_2$ gas. Additionally, a water cell regulated at ~35° C. is put in series with the "tall" TO-18 detector can. The 100% $CO_2$ present in the detector TO-18 can and the fixed amount of water vapor in the water cell serve to bias this second detector channel such that its output is completely independent of any amount of $CO_2$ and is only slightly responsive to the amount of water vapor in the sample chamber. This second detection channel serves as the biased reference for this NDIR gas sensing methodology.

The third detection channel comprises a thermopile detector packaged in the same custom-designed "tall" TO-18 can hermetically filled with 100% $CO_2$ gas. The 100% $CO_2$ present in the TO-18 detector can serves to bias this third detector channel such that its output is completely independent of any amount of $CO_2$ present in the sample chamber.

Using $CO_2$ gas alone in the sample chamber, the outputs from the first and third detection channels are used to generate a calibration curve A for $CO_2$. Calibration curve A alone cannot be used to measure $CO_2$ gas concentration in the sample chamber as the result is subjected to $H_2O$ interference.

Using $H_2O$ vapor alone in the sample chamber, the outputs from first and second detection channels are used to generate a calibration curve B for $H_2O$. Calibration curve B alone cannot be used to measure $H_2O$ vapor concentration in the sample chamber as the result is subjected to $CO_2$ interference.

Again using $H_2O$ alone in the sample chamber, the outputs of the second and third detection channels are used to generate a calibration curve C which can be used to measure $H_2O$ concentration in the sample chamber free from $CO_2$ interference.

Calibration curves A, B and C can are normalized (by comparison to a normalization value obtained by non-absorbing nitrogen) to create normalized calibration curves NA, NB and NC.

When the data used to generate calibration curves A, B and C is obtained, either $CO_2$ gas alone or $H_2O$ vapor alone is used to generate the data. What this means is not that no other gases will be present with the exception of nitrogen when such data is generated. $CO_2$ gas alone or $H_2O$ vapor alone at known concentrations (balanced to atmospheric pressure with dry nitrogen) will be fed into the gas sample chamber and the known concentrations of these gases in the sample chamber will be used to generate the data which is then used to generate the calibration curves.

Normalized calibration curves NA and NB are multiplied to generate a combined calibration curve ND. By using the previously generated normalized calibration curve NC to first determine the amount of $H_2O$ in the sample chamber independent of any $CO_2$ present, calibration curve ND can then be used to determine the amount of $CO_2$ that is in the sample chamber even in the simultaneous presence of interfering $H_2O$.

Because all three detection channels have the same narrow band pass spectral filter and they receive radiation from one single infrared source, they are all affected in the same way to first order when there are spectral changes caused by temperature variations in the sample chamber and/or by the short or long term operational changes of the infrared source. Thus, the outputs of the dual-channel NDIR gas sensor for the detection of $CO_2$ and $H_2O$ implemented using the presently invented Crossed Biased Filtering methodology will stay drift-free over time without the need for any periodic re-calibration or software correction.

The present invention will now be described by reference to FIGS. 1-8.

FIG. 1 shows the spectral locations of the $CO_2$ (101) and $H_2O$ (102) infrared absorption bands at around 2.70µ. One can see from FIG. 1 that the two absorptions bands are in no way identical, although there is a significant overlap of spectral features between them. FIG. 1 also shows the spectral characteristics of a narrow band pass spectral filter, 103, with CWL=2.70µ and FWHM=0.20µ (shaded area) to be used in the presently invented methodology. This spectral filter, 103, is capable of detecting both the $CO_2$ and $H_2O$ gases in the sample chamber albeit to different extents.

Figure 2:
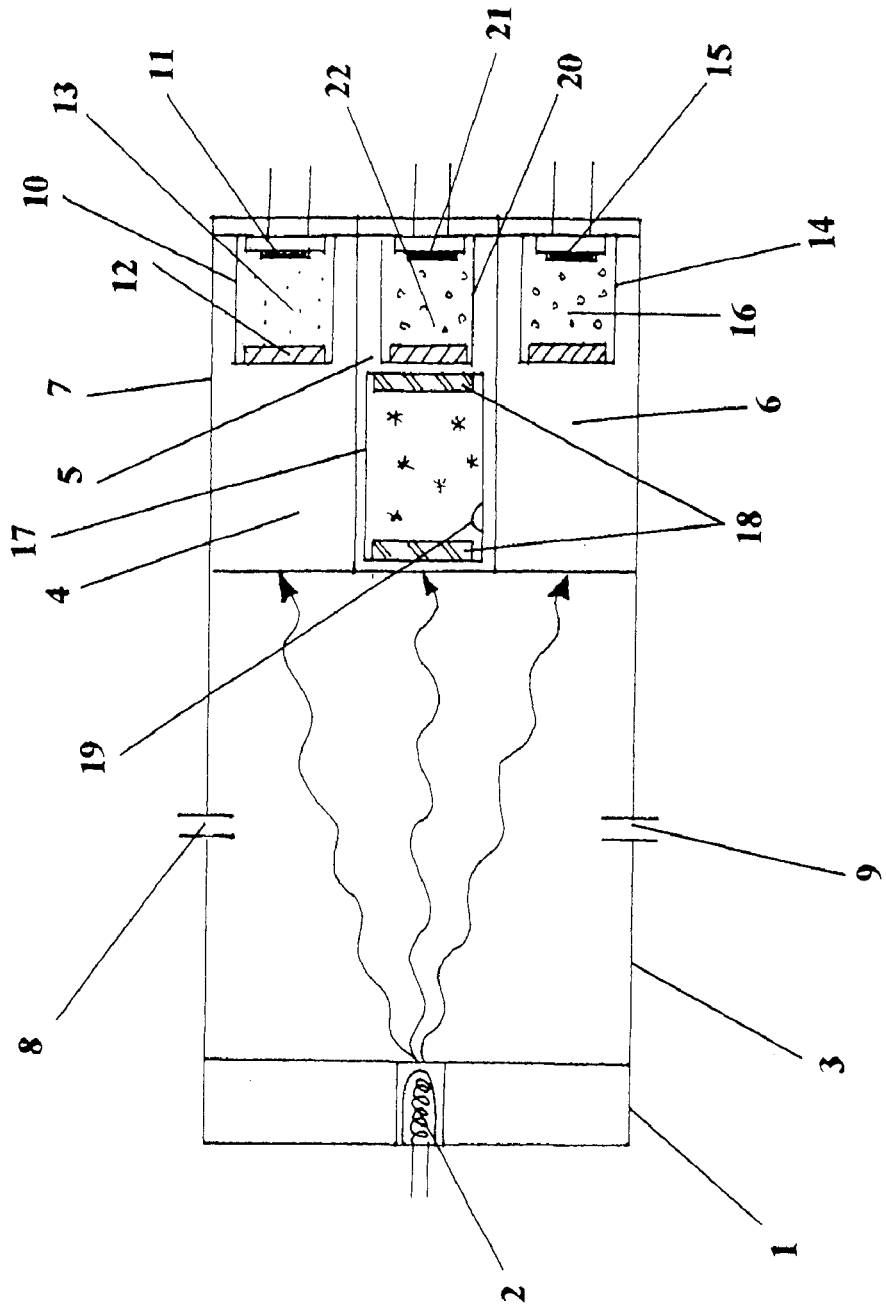
FIG. 2 depicts the schematic components layout for the presently invented methodology.
Figure 3:
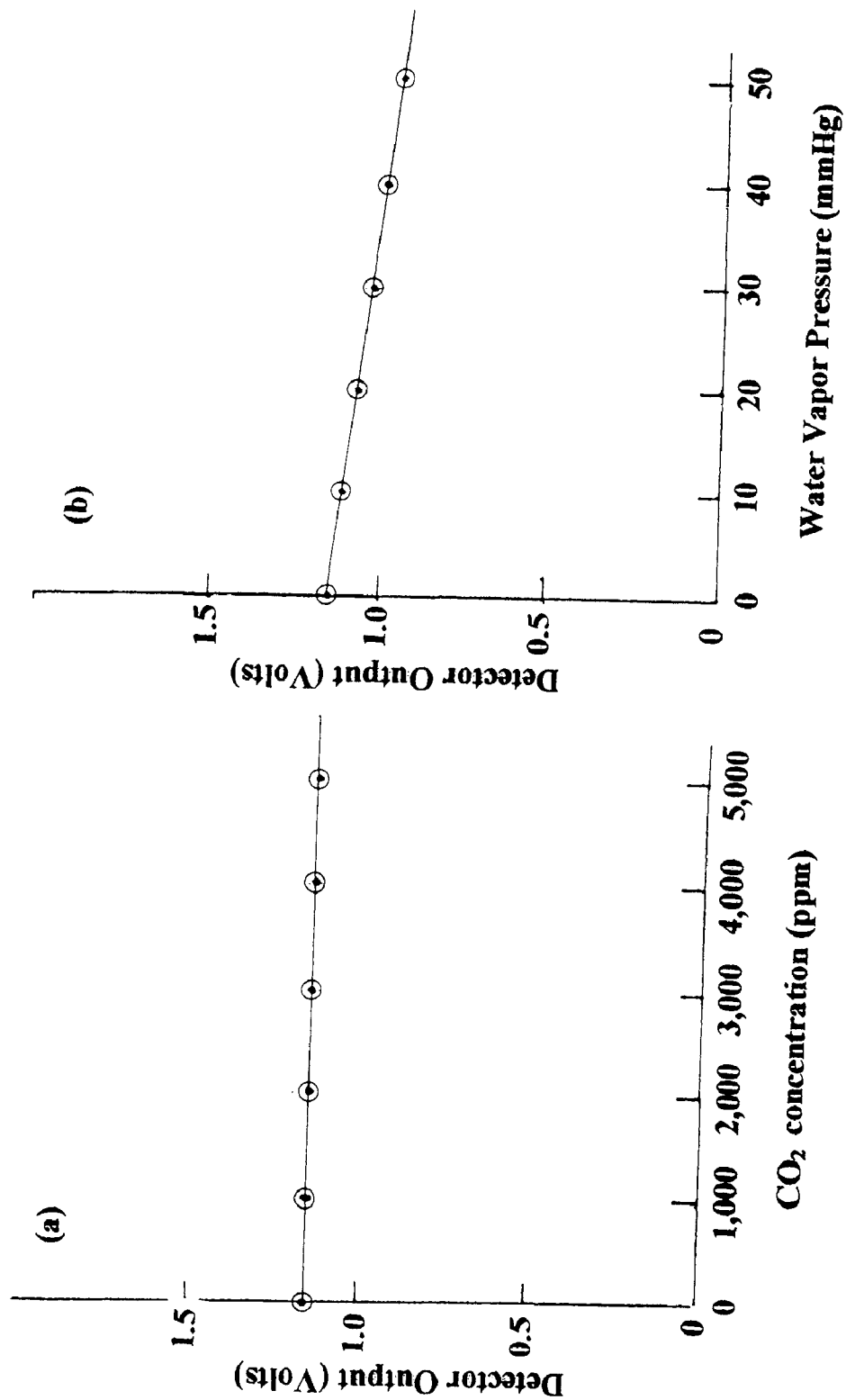
FIG. 3 depicts (a) the detector output of the crossed biased filtering channel as a function of $CO_2$ in the sample chamber and (b) the same detector output as a function of $H_2O$ in the sample chamber.
Figure 4:
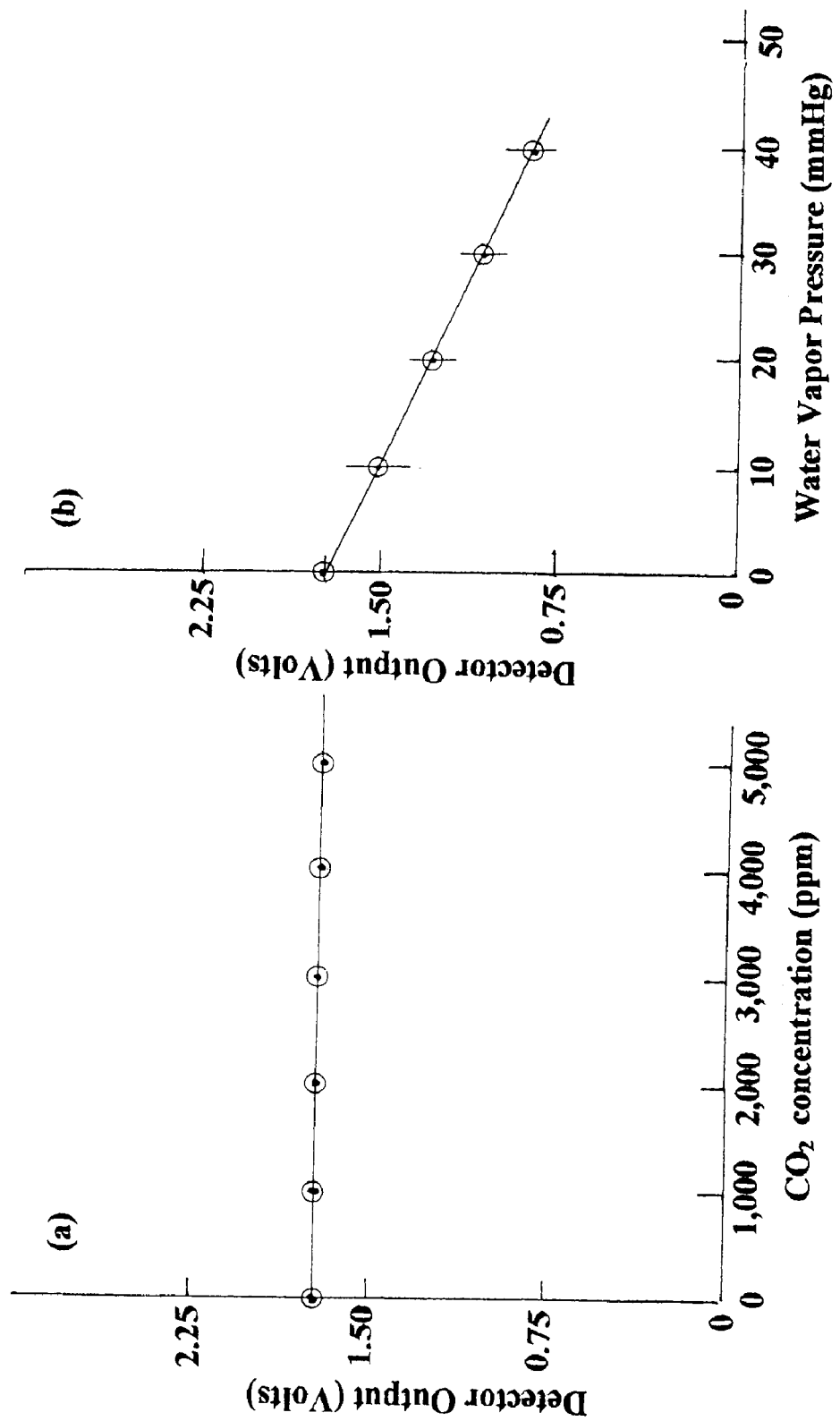
FIG. 4 depicts (a) the detector output of the secondary signal channel as a function of $CO_2$ in the sample chamber and (b) the same detector output as a function of $H_2O$ in the sample chamber.

FIG. 2 shows schematically the components layout for the presently invented Crossed Biased Filtering (CBF) methodology for NDIR gas sensors. The layout comprises three compartments for the dual-gas detection sensor. The infrared source compartment 1 houses the infrared source 2 shown as a miniature incandescent light bulb. The sample chamber compartment 3 directs the radiation emanating from the light bulb 2 into three respective detection channels 4, 5 and 6 which together constitute the detector compartment 7. A small opening 8 located on one side and another small opening 9 located on the opposite side of the sample chamber 3 serve to let air samples into and out of same in a diffusion mode of gas detection.

The first detection channel 4 is the main signal channel consisting of a tall TO-18 detector package 10 housing a thermopile detector 11 with a narrow band pass filter (CWL=2.70µ and FWHM=0.20µ) hermetically sealed in 100% nitrogen atmosphere 13. The third detection channel 6 is the secondary signal channel consisting also of a tall TO-18 detector package 14 housing a thermopile detector 15 with the same spectral narrow band pass filter 12 as in detector package 10 but hermetically sealed in 100% $CO_2$ atmosphere 16.

The second detection channel 5 is the crossed biased reference channel consisting of two components. At the front is a water cell 17 with hermetically sealed borosilicate gas windows 18 with a tiny amount of liquid water 19 hermetically entrapped inside. At the back is another tall TO-18 detector package 20 housing a thermopile detector 21 with the same spectral narrow band pass filter 12 as in detector packages 10 and 14 but hermetically sealed in 100% $CO_2$ atmosphere 22.

As configured in FIG. 2, the output of detector 11 of the first detection channel 4 is a function of the presence of both $CO_2$ and $H_2O$ present in sample chamber 3. The output of detector 15 of third detection channel 6 is a function only of the presence of $H_2O$ in sample chamber 3. This is because of the fact that since the tall TO-18 can is hermetically filled with 100% $CO_2$ with ~0.5 cm path length, the absorber concentration of the entrapped $CO_2$ gas is sufficient to remove all pertinent $CO_2$ absorption radiation from the infrared source 2 thereby rendering the detector output independent of any additional $CO_2$ in the sample chamber 3.

The output of detector 21 of the second or the crossed biased channel 5 is independent of the presence of $CO_2$ and only mildly dependent on $H_2O$ in the sample chamber 3. This is because of the fact that the tall TO-18 can package 20 housing the detector 21 is filled with 100% $CO_2$ and the water cell is permanently entrapped with ~42 mmHg of water vapor pressure when it is temperature regulated at ~35° C. Similar to the case for the third detection channel 6, the amount of $CO_2$ entrapped in detector package 20 is sufficient to render the detector output to be independent of the presence of any additional $CO_2$ in the sample chamber 3. However, the amount of water vapor entrapped in the water cell 17 is only sufficient to bias the detector output to be only slightly dependent upon the presence of $H_2O$ in the sample chamber 3.

FIGS. 3(a) and 3(b) show, respectively, the detector output for the second or crossed biased filtering channel 5 as a function of $CO_2$ and $H_2O$ concentrations in the sample chamber 3 (see FIG. 2). One can see from FIG. 3(a) that the detector output is independent of the $CO_2$ concentration from 0 ppm (or 100% dry nitrogen) to 5,000 ppm in dry nitrogen (balanced at one atmosphere pressure). One can also see from FIG. 3(b) that the detector output is slightly dependent upon the presence of $H_2O$ in the sample chamber 3 and is slowly decreasing from 0 mmHg (or 100% dry nitrogen) to ~40 mmHg of water vapor pressure in same.

FIGS. 4(a) and 4(b) show, respectively, the detector output for the third detection channel 6 as a function of $CO_2$ and $H_2O$ concentrations in the sample chamber 3 (see also FIG. 2). One can see from FIG. 4(a) that the detector output is independent of the $CO_2$ concentration from 0 ppm to 5,000 ppm in sample chamber 3. One can also see from FIG. 4(b) that the detector output is a relatively strong function of the H2O gas present from 0 mmHg to ~40 mmHg in sample chamber 3.

Figure 5:
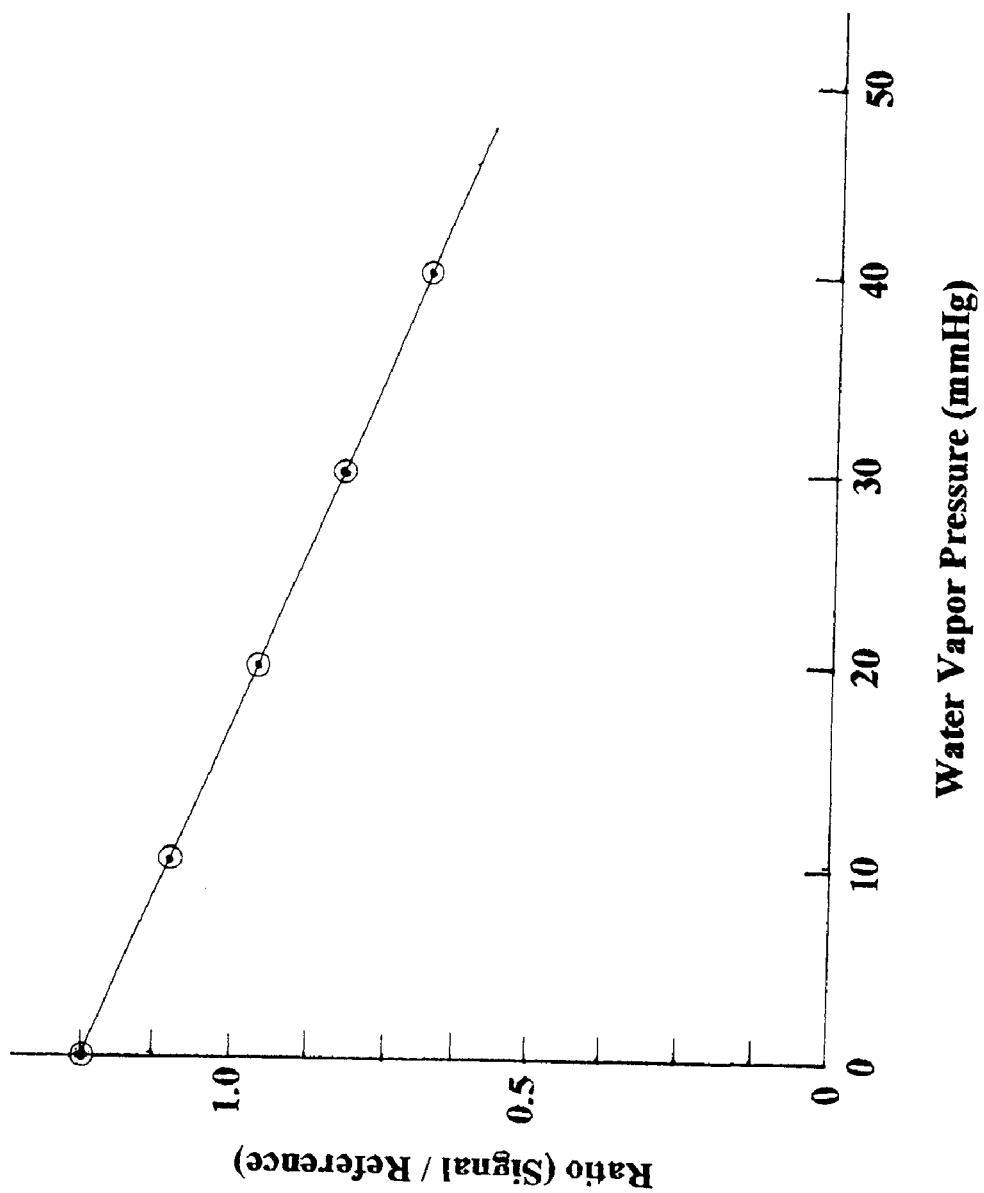
FIG. 5 depicts a calibration curve C for $H_2O$ in the sample chamber using the ratio of the detector outputs of the crossed biased filtering and the secondary signal channels.
Figure 6:
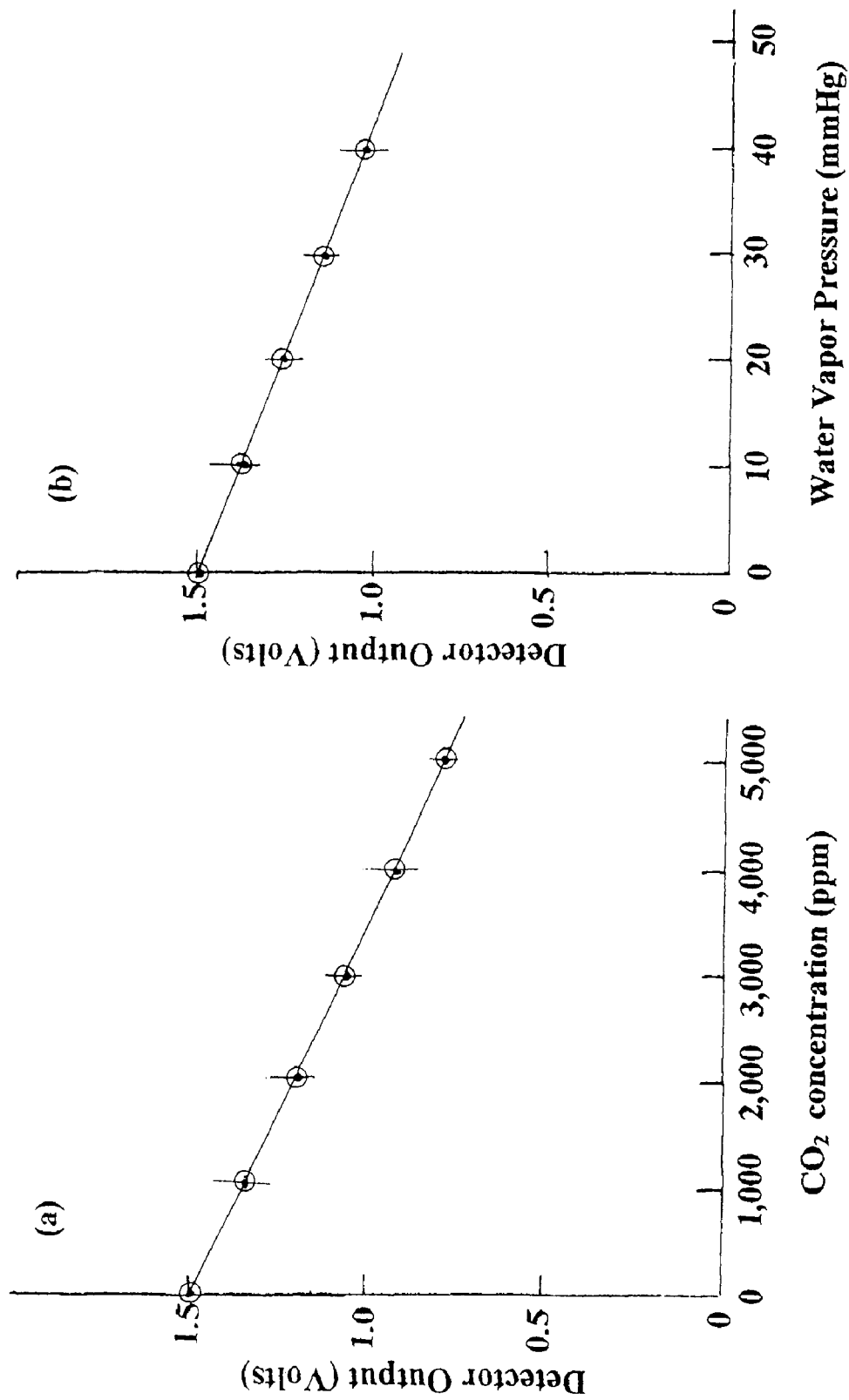
FIG. 6 depicts (a) the detector output of the main signal channel as a function of $CO_2$ alone in the sample chamber and (b) the same detector output as a function of $H_2O$ alone in the sample chamber.

By combining the detector output versus $H_2O$ concentration in sample chamber 3 in the third detection channel 6 as "signal" as depicted in FIG. 4(b) and the detector output versus $H_2O$ concentration in the sample chamber 3 in the second detection channel 5 as "reference" as depicted in FIG. 3(b), a calibration curve C is obtained by plotting the ratio of the value of "signal" over the value of "reference" against the $H_2O$ concentration in sample chamber 3 as shown in FIG. 5. This calibration curve C can be used to determine the $H_2O$ concentration in sample chamber 3 as a single NDIR gas sensor and free from the interference of $CO_2$ which might be simultaneously present in the sample chamber 3.

FIGS. 6(a) and 6(b) show, respectively, the detector output for the first detection channel 4 as a function of $CO_2$ only and $H_2O$ only concentration in sample chamber 3 (see also FIG. 2). One can see from FIGS. 6(a) and 6(b) that the detector output is a relatively strong function of either $CO_2$ or $H_2O$ individually present in sample chamber 3. But these calibration curves in FIGS. 6(a) and 6(b) cannot be used to determine the concentration of these gases when both of them are present in the sample chamber 3 due to mutual interferences.

Figure 7:
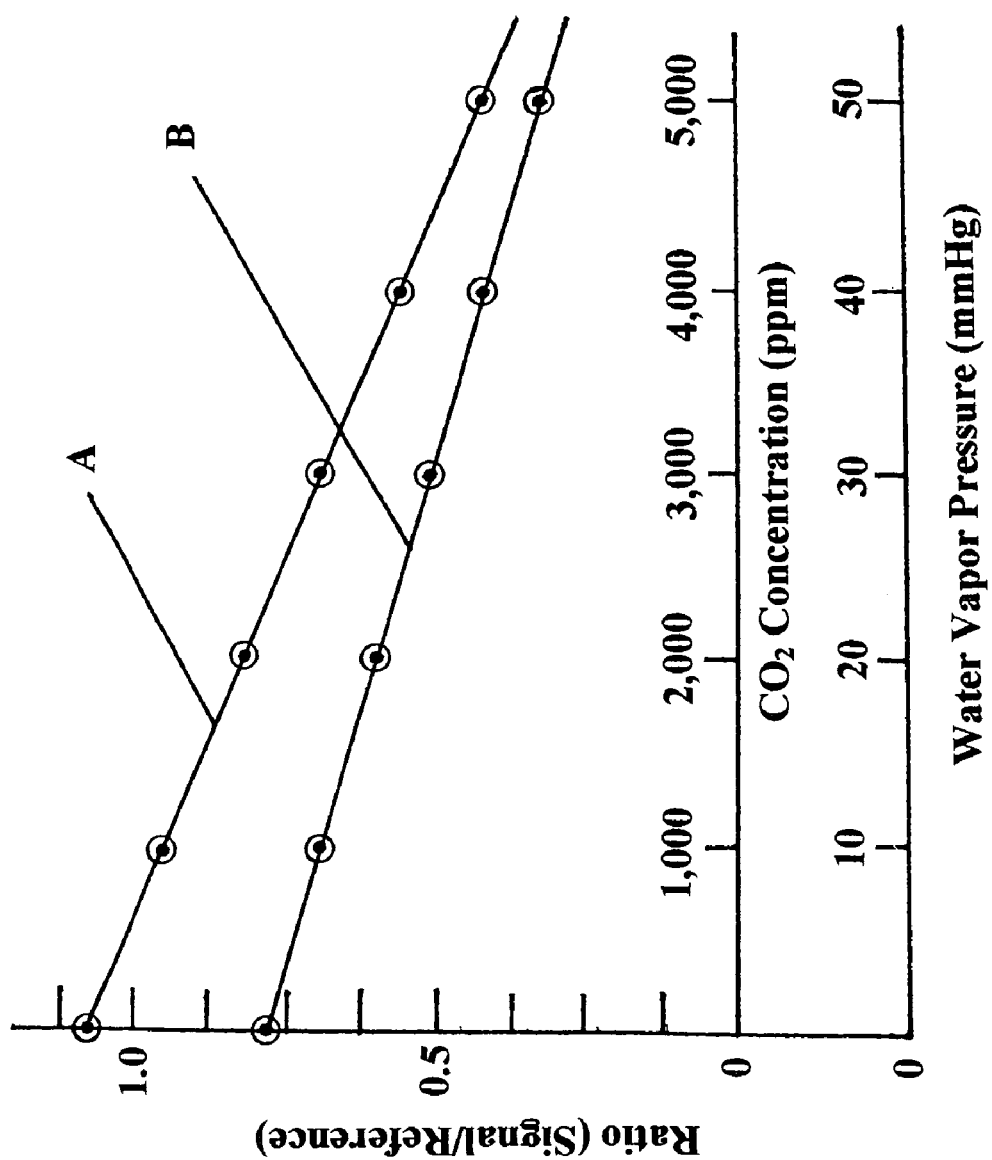
FIG. 7 depicts calibration curves for both $CO_2$ (curve A) and $H_2O$ (curve B) using the respective ratio of the detector outputs of the main signal and the crossed biased filtering channels.

By combining the output of the first detection channel 4 versus $CO_2$ alone present in sample chamber 3 as "signal" as depicted in FIG. 6(a) and the output of the second detection channel 5 versus $CO_2$ alone present in sample chamber 3 as "reference" as depicted in FIG. 3(a), a calibration curve A is obtained by plotting the ratio of the value of "signal" over the value of "reference" against $CO_2$ concentration alone in sample chamber 3 as shown in FIG. 7 as curve A. However, although this calibration curve A can be used to determine the $CO_2$ concentration in sample chamber 3 as a single NDIR gas sensor, its accuracy suffers severely whenever there is also $H_2O$ present in sample chamber 3 due to interference effects.

Similarly, by combining the output of the first detection channel 4 versus $H_2O$ alone present in sample chamber 3 as "signal" as depicted in FIG. 6(b) and the output of the second detection channel 5 versus $H_2O$ alone present in sample chamber 3 as "reference" as depicted in FIG. 3(b), a calibration curve B is obtained by plotting the ratio of the value of "signal" over the value of "reference" against $H_2O$ concentration alone in sample chamber 3 as also shown in FIG. 7 as curve B plotted side by side with its counterpart calibration curve A. Again, although this calibration curve B can be used to determine the $H_2O$ concentration in sample chamber 3 as a single NDIR gas sensor, its accuracy suffers severely whenever there is also $CO_2$ present in sample chamber 3 due to interference effects.

Figure 8:
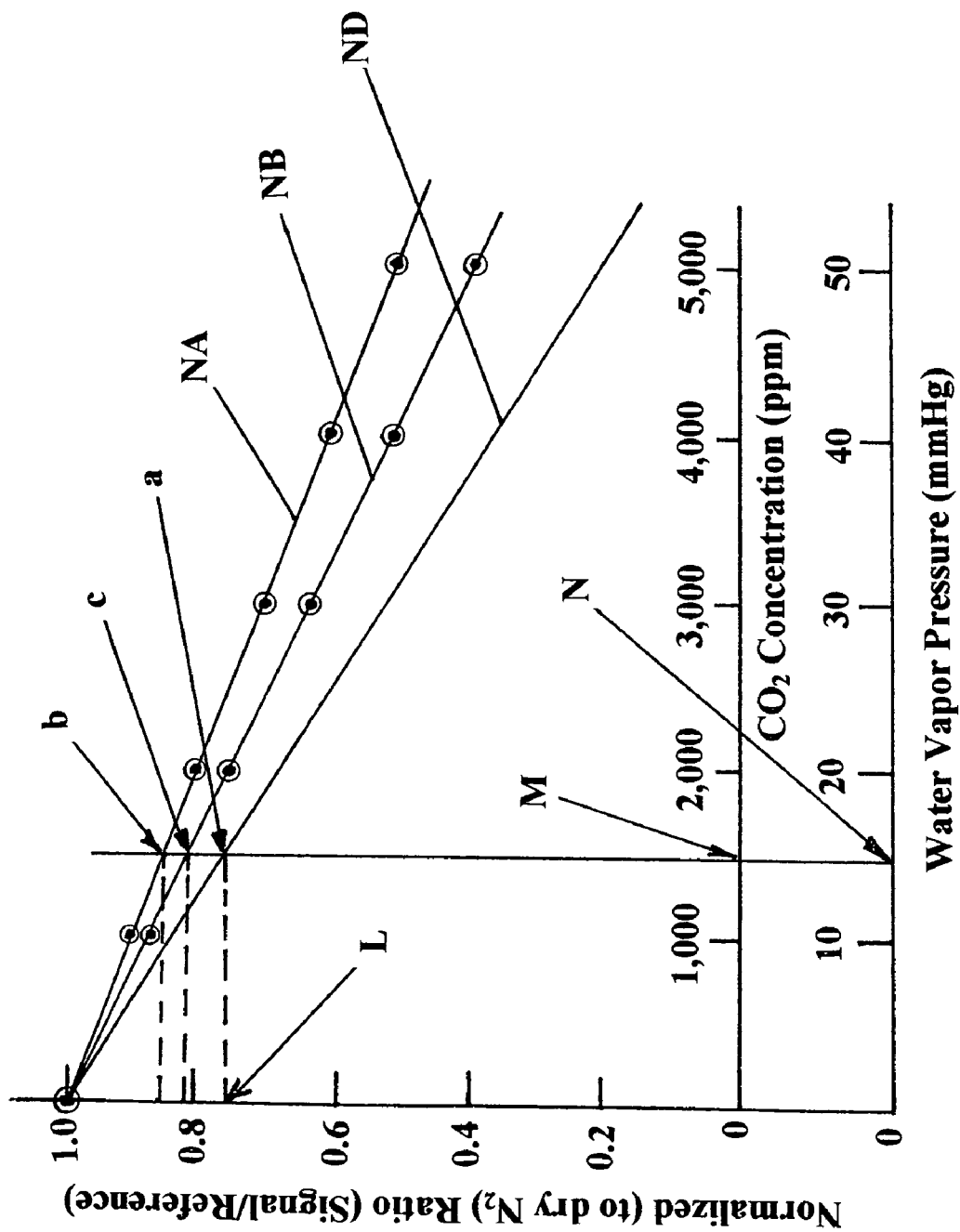
FIG. 8 depicts the normalized ratio for the calibration curves A and B respectively for $CO_2$ and $H_2O$ to generate a combined calibration curve ND for measuring the simultaneous presence of $CO_2$ and $H_2O$ in the sample chamber.

The calibration curves A and B portrayed in FIG. 7 can be used, respectively, for the detection of $CO_2$ and $H_2O$ present in sample chamber 3 albeit with mutual interference problems. The calibration curves A and B can be presented as normalized transmission efficiencies versus respective gas concentrations in sample chamber 3 as shown in FIG. 8. The normalizing factor used is the ratio of the value of "signal" over the value of "reference" as outputted respectively by the detectors when there is only dry nitrogen in the sample chamber 3. Thus, both calibration curves A and B start off with a value of unity when there is zero concentration of the respective gas in sample chamber 3 as shown in FIG. 8. This zero gas concentration condition is typically attained by simply allowing only dry 100% nitrogen flowing into and out of the sample chamber 3.

This particular manner of representing the calibration curves for both $CO_2$ and $H_2O$ allows a combined calibration curve ND to be constructed from the individual calibration curves NA and NB for the respective gases. It is done by simply multiplying the normalized transmission efficiencies for the two gases respectively at a particular concentration of their combined presence in sample chamber 3. Thus, referring to FIG. 8, the value L for point a on the normalized calibration curve ND for the combined presence of M ppm of $CO_2$ and N mmHg of $H_2O$ in sample chamber 3 is simply the product of the values for b and c, namely L=b×c, where b is read from normalized calibration curve NA for M ppm of $CO_2$ and c is read from normalized calibration curve NB for N mmHg of $H_2O$, both gases being in the sample chamber 3 together.

Conversely, let us assume that for a particular combined presence of $CO_2$ and $H_2O$ in sample chamber 3, the normalized transmission efficiency value is measured by the first detection channel 4 to be L. At the same time, if we can also measure independently the normalized transmission efficiency of $H_2O$ to be c (obtained from FIG. 5 after ratio normalization), one of the two gases in the sample chamber 3, then we can determine the normalized transmission efficiency for $CO_2$ which is given by c=L/b. Once b is known, we can calculate the value for the concentration of $CO_2$ present in sample chamber 3 using normalized curve ND of FIG. 8.

But earlier we have already shown that by using the third detection channel 6 and the second detection or crossed biased filtering channel 5 we can obtain independently a calibration curve C (see FIG. 5) for $H_2O$ concentration which is free from any interference effects caused by the presence of $CO_2$ in sample chamber 3. In other words, with the use of the outputs from the first detection channel 4 and the second detection channel 5 to generate a combined $CO_2$ and $H_2O$ calibration curve ND of FIG. 8, and the use of the outputs from the third detection channel 6 and again the second detection channel 5 to determine a calibration curve for $H_2O$ (see FIG. 5) which is free from the interference of $CO_2$ in sample chamber 3, both the concentrations of $CO_2$ and $H_2O$ can be determined using the presently invented methodology.

Furthermore, since all three channels, namely the first, second and third detection channels, all use the same narrow band pass filter 12 of FIG. 2(CWL=2.70μ and FWHM=0.20μ) for the selection of radiation from the infrared source, they effectively use the Saturated Filtering Reference (SFR) methodology for NDIR gas sensors disclosed earlier for achieving zero-drift or thermostat-like behavior in their performance.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A Non-Dispersive Infrared ("NDIR") gas sensor, comprising:
    an infrared source compartment containing an infrared source;
    a sample chamber;
    a detector compartment, said sample chamber being located optically between the infrared source compartment and the detector compartment, said detector compartment comprising:
        a first detection channel comprising a first narrow band pass filter hermetically sealed with a non-absorbing gas that does not have an absorption band overlapping a first gas or water vapor, said first detection channel having a first output modulated by presence of the first gas and water vapor in the sample chamber;
        a second detection channel comprising a second narrow band pass filter hermetically sealed with the first gas and a water cell located optically between the infrared source and the second narrow band pass filter, said second detection channel having a second output that is independent of any amount of the first gas in the sample chamber and partially responsive to the amount of the water vapor in the sample chamber; and
        a third detection channel comprising a third narrow band pass filter hermetically sealed with the first gas, said third detection channel having a third output that is independent of the amount of the first gas in the sample chamber; and
    electronics for processing signals from the first detection channel, the second detection channel and the third detection channel and for calculating a detected concentration of the first gas in a gas sample comprising a combination of the first gas and water vapor in the sample chamber based upon the first output, the second output, the third output and a set of calibration data for the NDIR gas sensor; and
    wherein the first narrow band pass filter, the second narrow band pass filter and the third narrow band pass filter have a central wavelength and a full width half-maximum bandwidth that are identical and the central wavelength falls within an absorption band of the first gas and water vapor.

2. The NDIR gas sensor of claim 1 wherein the set of calibration data is comprised of a calibration curve A generated by dividing the first output by the second output when the first gas alone is present in the sample chamber, a calibration curve B generated by dividing the first output by the second output when water vapor alone is present in the sample chamber, and a calibration curve C generated by dividing the third output by the second output when water vapor alone is present in the sample chamber.

3. The NDIR gas sensor of claim 2 wherein the calibration curve A plots a ratio of the first output divided by the second output against the first gas concentration alone in the sample chamber, the calibration curve B plots a ratio of the first output divided by the second output against water vapor concentration alone in the sample chamber, and the calibration curve C plots a ratio of the third output divided by the second output against water vapor concentration alone in the sample chamber.

4. The NDIR gas sensor of claim 2 wherein the set of calibration data is further comprised of a calibration curve NA generated by normalizing the calibration curve A and a calibration curve NB generated by normalizing the calibration curve B.

5. The NDIR gas sensor of claim 4 wherein the electronics calculates the detected concentration of the first gas in the gas sample in the sample chamber when the first output has a value "a," the second output has a value "b" and the third output has a value "c" by a method comprising:
    normalizing the first output value "a" to obtain a normalized first output value "a'";
    dividing the third output value "c" by the second output value "b" to obtain a value "d";
    using the value "d" and the calibration curve C to obtain a water vapor content "e" in the gas sample;
    using the water vapor content "e" and the calibration curve NB to obtain a value "f";
    dividing the value "a'" by the value "f" to obtain a value "g";
    using a calibration curve ND and the value "g" to obtain the detected concentration of the first gas in the gas sample;
    wherein the calibration curve ND is generated by multiplying together the calibration curves NA and NB.

6. The NDIR gas sensor of claim 5 wherein value "a" is normalized by dividing value "a" by a value "$a_0$" obtained as the first output when the non-absorbing gas alone is present in the sample chamber.

7. The NDIR gas sensor of claim 6 wherein the non-absorbing gas is comprised of nitrogen.

8. A process for detecting a concentration of a first gas in the presence of water vapor when the first gas and water vapor have overlapping absorption bands and the first gas and water vapor are in a gas sample of a gas chamber of an Non-Dispersive Infrared ("NDIR") gas sensor having a first detection channel, a second detection channel and a third detection channel, all of the first, the second and the third detection channels having a narrow band pass filter with a central wavelength and a full width half-maximum bandwidth that are identical and the central wavelength falls within an absorption band of the first gas and water vapor, said process comprising:

measuring a first output of the first detection chamber that is modulated by the presence of both the first gas and water vapor in the sample chamber;

measuring a second output of the second detection chamber that is independent of any concentration of the first gas and only slightly responsive to an amount of water vapor in the sample chamber;

measuring a third output of the third detection chamber that is independent of an concentration of the first gas in the sample chamber; and using the first, the second and the third outputs to calculate the concentration of the first gas through use of a set of calibration data for the NDIR sensor.

9. The process of claim 8, wherein the set of calibration data is comprised of a calibration curve A generated by dividing the first output by the second output when the first gas alone is present in the sample chamber, a calibration curve B generated by dividing the first output by the second output when water vapor alone is present in the sample chamber, and a calibration curve C generated by dividing the third output by the second output when water vapor alone is present in the sample chamber.

10. The process of claim 9 wherein the calibration curve A plots a ratio of the first output divided by the second output against the first gas concentration alone in the sample chamber, the calibration curve B plots a ratio of the first output divided by the second output against water vapor concentration alone in the sample chamber, and the calibration curve C plots a ratio of the third output divided by the second output against water vapor concentration alone in the sample chamber.

11. The process of claim 9 wherein the set of calibration data is further comprised of a calibration curve NA generated by normalizing the calibration curve A and a calibration curve NB generated by normalizing the calibration curve B.

12. The process of claim 11 wherein the first output has a value "a", the second output has value "b" and the third output has a value "c" for the gas sample.

13. The process of claim 12 wherein the concentration of the first gas in the gas sample is calculated by a method comprising:

normalizing the first output value "a" to obtain a normalized first output value "a'";

dividing the third output value "c" by the second output value "b" to obtain a value "d";

using the value "d" and the calibration curve C to obtain a water vapor content "e" in the gas sample;

using the water vapor content "e" and the calibration curve NB to obtain a value "f";

dividing the value "a'" by the value "f" to obtain a value "g"; and using a calibration curve ND and the value "g" to obtain the detected concentration of the first gas in the gas sample;

wherein the calibration curve ND is generated by multiplying together the calibration curves NA and NB.

14. The NDIR gas sensor of claim 13 wherein value "a" is normalized by dividing value "a" by a value "$a_0$" obtained as the first output when the non-absorbing gas alone is present in the sample chamber.

15. The NDIR gas sensor of claim 14 wherein the non-absorbing gas is comprised of nitrogen.

16. The process of claim 8, wherein the first detection channel is comprised of a first narrow band pass filter hermetically sealed with a non-absorbing gas that does not have an absorption band overlapping the first gas or water vapor; the second detection channel is comprised of a second narrow band pass filter hermetically sealed with the first gas and a water cell located optically between an infrared source and the second narrow band pass filter; and the third detection channel is comprised of a third narrow band pass filter hermetically sealed with the first gas.

17. A process, comprising:

generating a calibration curve A by plotting a ratio of a first output of a Non-Dispersive Infrared ("NDIR") gas sensor divided by a second output of the NDIR gas sensor versus concentration of a first gas alone when the first and the second outputs are detected using the first gas alone in a sample chamber, wherein the NDIR gas sensor is comprised of:

an infrared source compartment containing an infrared source;

the sample chamber;

a detector compartment, said sample chamber being located optically between the infrared source compartment and the detector compartment, said detector compartment comprising:

a first detection channel comprising a first narrow band pass filter hermetically sealed with a non-absorbing gas that does not have an absorption band overlapping the first gas or water vapor, said first detection channel having the first output modulated by presence of the first gas and water vapor in the sample chamber;

a second detection channel comprising a second narrow band pass filter hermetically sealed with the first gas and a water cell located between the infrared source and the second narrow band pass filter, said second detection channel having the second output that is independent of any amount of the first gas in the sample chamber and partially responsive to the amount of water vapor in the sample chamber; and a third detection channel comprising a third narrow band pass filter hermetically sealed with the first gas, said third detection channel having a third output that is independent of the amount of the first gas in the sample chamber; and electronics for processing signals from the first detection channel, the second detection channel and the third detection channel;

wherein the first narrow band pass filter, the second narrow band pass filter and the third narrow band pass filter have a central wavelength and a full width half-maximum bandwidth that are identical and the central wavelength falls within an absorption band of the first gas and water vapor;

generating a calibration curve B by plotting a ratio of the first output divided by the second output versus concentration of water vapor alone when the first and the second outputs are detected using water vapor alone in the sample chamber;

generating a calibration curve C by plotting a ratio of the third output divided by the second output versus concentration of water vapor alone when the second and the third outputs are detected using water vapor alone in the sample chamber;

generating a normalized calibration curve NA by normalizing the calibration curve A with only the non-absorbing gas in the sample chamber;

generating a normalized calibration curve NB by normalizing the calibration curve B with only the non-absorbing gas in the sample chamber;

generating a calibration curve ND by multiplying together calibration curves NA and NB;

obtaining an output "a" for a gas sample in the sample chamber from the first detection channel;

obtaining an output "b" for the gas sample from the second detection channel;

obtaining an output "c" for the gas sample from the third detection channel; and calculating a detected concentration of the first gas in the gas sample by use of the outputs "a," "b" and "c" and the calibration curves C, NB and ND.

* * * * *